United States Patent [19]
Nikutowski et al.

[11] Patent Number: 5,288,230
[45] Date of Patent: Feb. 22, 1994

[54] COATED ORTHODONTIC ARCHWIRE

[75] Inventors: Enrique A. Nikutowski, Monrovia; Randall E. Adam, Temple City, both of Calif.; David G. O'Neill, Woodbury, Minn.

[73] Assignee: Minnesota Mining and Manufacturing Company, St. Paul, Minn.

[21] Appl. No.: 11,373

[22] Filed: Jan. 29, 1993

Related U.S. Application Data

[62] Division of Ser. No. 732,117, Jul. 18, 1991, Pat. No. 5,203,804.

[51] Int. Cl.$^5$ .............................................. A61C 3/00
[52] U.S. Cl. .................................................... 433/20
[58] Field of Search ...................... 423/10, 20, 21, 22, 423/8

[56] References Cited

U.S. PATENT DOCUMENTS

| | | | |
|---|---|---|---|
| 2,562,587 | 7/1981 | Swearing | 51/309 |
| 2,697,878 | 12/1954 | Oberley | 32/59 |
| 3,504,438 | 4/1970 | Wittman et al. | 32/14 |
| 3,717,932 | 2/1973 | Brainin | 32/10 A |
| 4,050,156 | 9/1977 | Chasanoff et al. | 32/2 |
| 4,190,958 | 3/1980 | Martin et al. | 433/102 |
| 4,526,541 | 7/1985 | Hubschmid | 433/165 |
| 4,626,209 | 12/1986 | Tsai et al. | 433/9 |
| 4,722,689 | 2/1988 | Corbett | 433/218 |
| 4,780,079 | 10/1988 | Kato et al. | 433/2 |
| 4,902,224 | 2/1990 | Collins et al. | 433/8 |
| 4,946,387 | 8/1990 | Adell | 433/20 |
| 5,032,080 | 7/1991 | Hakansson et al. | 433/8 |

FOREIGN PATENT DOCUMENTS

| | | |
|---|---|---|
| 3519213A1 | 6/1986 | Fed. Rep. of Germany . |
| 3620444A1 | 3/1988 | Fed. Rep. of Germany . |
| 59-82851 | of 1984 | Japan . |
| 1-256949 | 10/1989 | Japan . |

OTHER PUBLICATIONS

"Ion Beam and Plasma Methods of Producing Diamondlike Carbon Films", Swec et al., NASA Technical Memorandum No. 102301, 1988.

"Properties of the Diamond–like Carbon Film Produced by the Condensation of a Plasma Stream with an rf Potential", Strel'nitskii et al., *Sov. Phys. Techn. Phys.*, 23(2) Feb. 1978.

"An Artificial Oral Environment for Testing Dental Materials", DeLong et al., *IEEE Transactions on Biomedical Engineering*, vol. 38, No. 4, Apr. 1991.

"Biodegradation of Orthodontic Appliances and Their Effects on the Blood Level of Nickel and Chromium", Thesis by Robert Barrett, University of Iowa, May, 1990.

"Status and Applications of Diamond and Diamond-like Materials: An Emerging Technology", National Materials Advisory Board, National Academy Press, 1990.

"Diamond and Diamondlike Films: Deposition Processes and Properties", Deshpandey et al., *J. Vac. Sci. Technol.* A 7(3), May/Jun. 1989.

"Low-Pressure, Matastable Growth of Diamond and 'Diamondlike' Phases", Angus et al., *Science*, vol. 241, pp. 913–921, Aug. 19, 1988.

*Primary Examiner*—John J. Wilson
*Assistant Examiner*—Nicholas D. Lucchesi
*Attorney, Agent, or Firm*—Gary L. Griswold; Walter N. Kirn; James D. Christoff

[57] ABSTRACT

An orthodontic archwire is coated with a hard carbon coating of polycrystalline diamond, diamond-like amorphous hydrogen-free carbon, diamond-like hydrogenated amorphous carbon, or combinations thereof. The hard carbon coating presents a barrier to nickel and chromium that might otherwise diffuse from an underlying metal substrate, and as such is useful for patients exhibiting sensitivity to nickel and chromium.

12 Claims, 2 Drawing Sheets

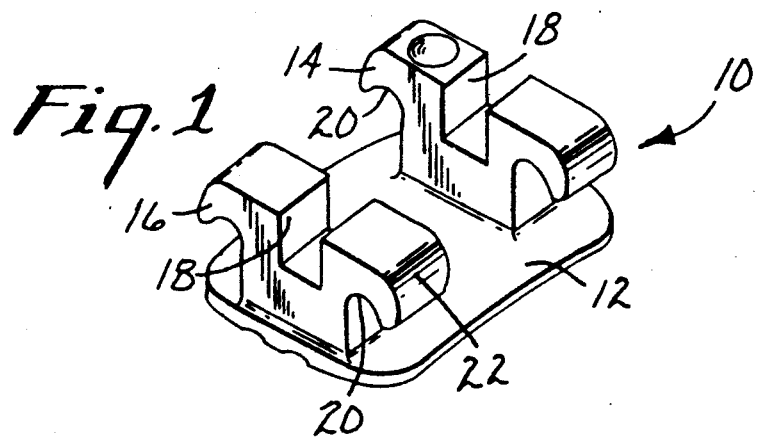
Fig. 1
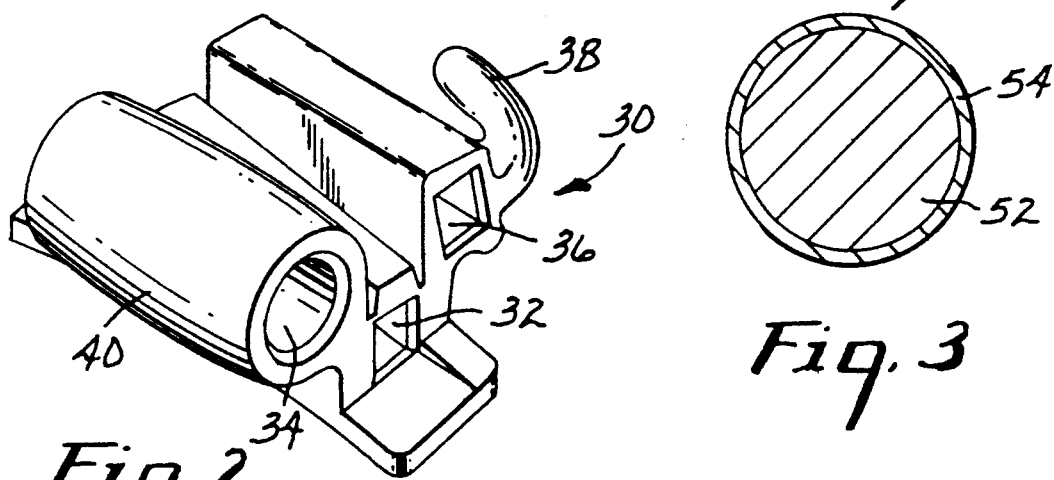
Fig. 2
Fig. 3
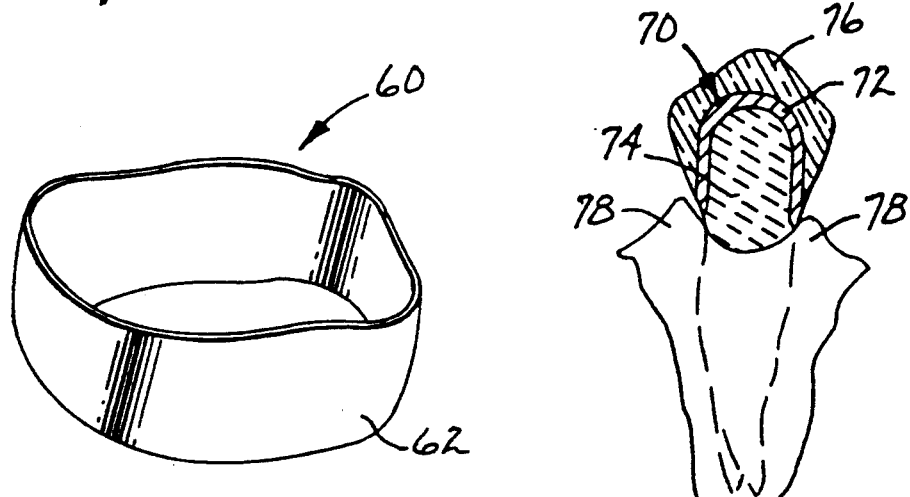
Fig. 4
Fig. 5

COATED ORTHODONTIC ARCHWIRE

This is a division of application Ser. No. 07/732,117 filed Jul. 18, 1991 now U.S. Pat. No. 5,203,804.

BACKGROUND OF THE INVENTION

1. Field of the Invention

This invention relates to a dental article such as an orthodontic bracket, orthodontic arch wire, or crown substrate having one or more surfaces covered with a hard, relatively thin carbon coating.

2. Description of the Related Art

Metal alloys are widely used to make articles for dental treatment. For example, stainless steel is commonly used to make tooth brackets, buccal tubes, arch wires and bands for orthodontic treatment. Other alloys are used for substrates that serve as bases or copings for porcelain in making a crown.

Often, metal alloys used for dental articles are exposed in the oral cavity and come into contact with oral mucosa and saliva for extended periods of time. Orthodontic brackets, for example, are mounted over external tooth surfaces and are generally in continuous contact with saliva during treatment. Such brackets may also intermittently contact the patient's tongue or inner portions of the patient's cheeks or lips. Orthodontic buccal tubes, arch wires and bands are similarly exposed. The metal substrate of dental crowns and bridges is substantially covered by porcelain but is exposed at the margin next to the gingiva and as a result is in contact with saliva and sometimes the gingiva or other oral tissues.

It has been widely reported that certain metals cause an allergic reaction in a certain percentage of the population. These metals are commonly used in dental articles, and it is suspected that the metals diffuse from such dental articles into the patient and cause an allergic reaction in some patients. For instance, reports in the literature indicate that nickel is suspected of causing inflammation (and sometimes rashes or blisters) of oral tissue. Rapid loss of alveolar bone has been reported to be associated with the use of metal alloy crowns in patients with nickel hypersensitivity.

The concentration of nickel in dental articles often varies from manufacturer to manufacturer, and may also vary for different articles. Orthodontic appliances such as brackets, buccal tubes, bands and arch wires are commonly made of stainless steel having a nickel concentration ranging from 8 to 17 percent by weight. Metal substrates for dental crowns and bridges are often cast of an alloy having a nickel concentration of about 70 percent by weight. Some arch wires are made of a nickel-titanium alloy having a nickel content of 50 to 55 percent by weight.

Chromium in metal alloys of dental articles is also suspected to cause an allergic reaction in some patients. The chromium concentration in orthodontic stainless steel appliances often ranges from 17 to 20 percent by weight. The chromium concentration of alloys for crown and bridge substrates often ranges from 12 to 30 percent by weight.

Corrosion has also been reported as a significant problem in conventional dental articles made of metal alloys. Corrosion due to salts and acids in the oral cavity may corrode and pit the surface of metal dental articles, establishing locations where bacteria may accumulate. The accumulation of bacteria is particularly a problem in areas that cannot be reached by a toothbrush.

Dental articles are sometimes made of materials other than metal alloys containing nickel and chromium and can be used for patients sensitive to these elements. For instance, orthodontic brackets may be made of monocrystalline or polycrystalline alumina. However, stainless steel brackets are generally lower in cost than ceramic brackets and are preferred by many orthodontists. Ceramic brackets are also known to present higher frictional resistance to arch wires, a disadvantage in that the increased friction slows movement of the teeth and can lengthen treatment time.

Coating dental articles with a synthetic resinous material has previously been suggested. For example, U.S. Pat. No. 4,050,156 describes articles coated with a layer of para-oxybenzoyl homopolyester and polytetrafluoroethylene and a pigment for providing tooth coloring. Other aesthetic coatings made of polymeric materials are described in U.S. Pat. Nos. 3,504,438, 4,722,689 and 4,946,347.

Additionally, U.S. Pat. No. 4,626,209 describes an orthodontic bracket having a bonding base coated with a corrosion resistant metallic powder selected from the group consisting of stainless steel, nickel alloys, cobalt alloys, titanium and titanium carbide in order to enhance the bond of the base to the tooth. U.S. Pat. No. 4,902,224 describes an orthodontic bracket base that is coated with a siliceous material to enhance the adhesive bond to orthodontic cement. A tooth articulator described in U.S. Pat. No. 4,780,079 has a cobalt coating to kill bacteria.

While the patents identified above relate to coated dental articles, the problem of nickel or chromium diffusion from the alloy is not mentioned. There remains a need in the art for a coated dental article that is made of materials that are relatively inexpensive and yet reduces the likelihood of allergic reaction reportedly caused by conventional dental articles.

SUMMARY OF THE INVENTION

In accordance with the invention, a dental article is coated with a hard carbon coating. Preferably, the coating consists essentially of a polycrystalline diamond coating, a diamond-like amorphous hydrogen-free carbon coating, a diamond-like hydrogenated amorphous carbon coating, or combinations thereof.

It has been found that a continuous hard carbon coating in accordance with the invention provides a barrier that substantially prevents the diffusion of nickel and chromium from an underlying metal alloy to the surface of the coating. Consequently, the invention is useful for dental articles placed in patients who are sensitive to nickel and chromium. Additionally, the hard carbon coating when applied to orthodontic brackets and arch wires has been found to enhance the sliding mechanics between brackets and arch wires by lowering the coefficient of friction. The coating also provides resistance to corrosion of an underlying metal substrate that might otherwise occur during use in the oral cavity.

DETAILED DESCRIPTION OF THE DRAWINGS

FIG. 1 is a perspective view of a dental article according to one embodiment of the invention, wherein the article comprises an orthodontic bracket;

FIG. 2 is a perspective view of a dental article in accordance with another embodiment of the invention, wherein the article comprises an orthodontic buccal tube;

FIG. 3 is a cross-sectional view of a dental article according to another embodiment of the invention, wherein the article comprises an orthodontic arch wire;

FIG. 4 is a perspective view of a dental article in accordance with another embodiment of the invention, wherein the article comprises a tooth band;

FIG. 5 is a dental article in accordance with yet another embodiment of the invention, wherein the article comprises a crown or bridge substrate.

DETAILED DESCRIPTION OF THE PREFERRED EMBODIMENTS

Figure 6:
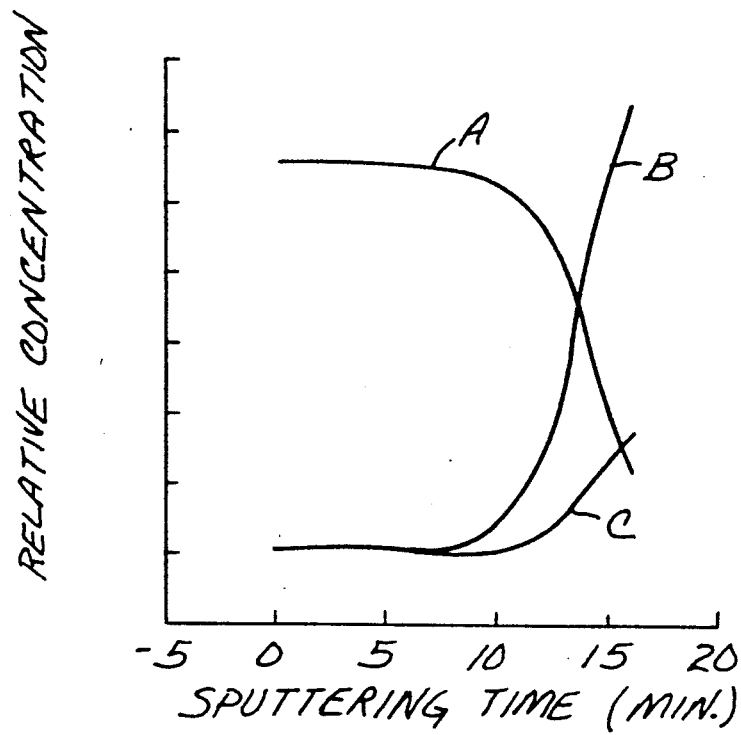
FIGS. 6–7 are graphs showing relative concentrations of carbon, nickel and chromium vs. sputtering time for unheated and heated samples having a hard carbon coating.

Coated dental articles according to various embodiments of the invention are shown in FIGS. 1–5. In each instance, the article includes a substrate that is covered by a thin coating of hard carbon that is substantially continuous, and preferably is continuous.

FIG. 1 illustrates an article of the invention that in this instance comprises a bracket 10 used in orthodontic treatment. The bracket 10 includes a base 12 adapted for direct bonding to a tooth surface, and twin tiewings 14, 16 are connected to the base 12. Each of the tiewings 14, 16 has a slot 18 to receive an arch wire. Recesses 20 behind each side of the tiewings 14, 16 are adapted to receive an elastomeric or a wire ligature that also straddles the arch wire in order to retain the arch wire in the slots 18.

The bracket 10 has an inner body or substrate that can be a cast or machined structure, but preferably is made using a sintering technique wherein the entire substrate is initially formed as a pressed "green" preform stainless steel powder, and then heated to a sintering temperature to yield the final product. The entire exterior surface of the bracket 10 is covered with a hard carbon coating 22 that will be described in more detail below.

In FIG. 2, a dental article according to another embodiment of the invention comprises a buccal tube 30 that is covered with a hard carbon coating 40. The buccal tube 30 is adapted to be secured to the molar teeth, and has a channel 32 to receive the ends of an arch wire. A round passage 34 next to the channel 32 is provided for receiving a headgear wire or a lip bumper wire, while a rectangular passage 36 on the opposite side of the channel 32 is adapted to receive a segmented arch wire. In addition, a hook 38 is provided for optional use of an interarch elastomeric force module to correct malocclusions.

The buccal tube 30 has a metal body or substrate beneath the outer coating 40. The substrate is preferably made using the sintering technique described above. The substrate of the buccal tube is somewhat similar to the buccal tube described in U.S. Pat. No. 4,927,362.

A coated dental article in FIG. 3 comprises an arch wire 50 used in orthodontic treatment in conjunction with brackets and buccal tubes such as the bracket 10 and the buccal tube 30. The arch wire 50 has a metal core or substrate 52 that is round in cross-section, and that is surrounded by a relatively thin hard carbon coating 54. Preferably, the substrate 52 is stainless steel or a nickel-titanium alloy.

FIG. 4 illustrates a coated dental article that comprises an orthodontic band 60 according to another embodiment of the invention. The band 60 includes a stainless steel substrate that is essentially the same as commercially available bands. The substrate is covered with a hard carbon coating 62. Bands such as band 60 are adapted to encircle the teeth and be cemented in place, and provide support for orthodontic brackets that are not directly bonded to teeth.

A coated dental article shown in FIG. 5 comprises a metal crown substrate 70 that is covered with a hard carbon coating 72. As illustrated, the substrate is shaped to receive a prepared tooth 74. An aesthetic porcelain layer 76 is bonded to the coating 72 to make a crown. The substrate 70 can also be used for a bridge.

Although the major extent of the coating 72 is covered by the porcelain layer 76, a gingival edge of the porcelain layer 76 is tapered and stops short of the gingival edge of the coating 72 covering the underlying portions of the substrate 70 to enable the dentist to seat the crown without undue injury to the gingiva. The coating 72 covers the gingival edge of the substrate 70 and provides a nickel and chromium barrier between the substrate 70 and the saliva or the gingiva 78.

The hard carbon coating of the article of the present invention means a polycrystalline diamond coating, a diamond-like amorphous hydrogen-free carbon coating, a diamond-like hydrogenated amorphous carbon coating or combinations thereof. The hard carbon coatings of this invention will generally show an intensity in the range of about 1300–1500 cm$^{-1}$ using Raman spectroscopy when the coating is at least about 0.15 microns thick.

Conventionally, diamond is characterized by $SP^3$ bonding between atoms and graphite is characterized by $SP^2$ bonding between atoms. Diamond-like materials exhibit both $SP^2$ and $SP^3$ bonding. The hard carbon coatings of the present invention will exhibit at least some $SP^3$ bonding.

A number of deposition processes may be utilized to coat a substrate, and are described in more detail in an article entitled "Diamond and diamondlike films: Deposition processes and properties", authored by C. V. Deshpandey and R. F. Bunshah (J. Vac. Sci. Technol. A, Vol. 7, No. 3, May/Jun 1989). These techniques include chemical vapor deposition processes including chemical transport method, hot filament thermal chemical vapor deposition (CVD) techniques, and electron assisted chemical vapor deposition (EACVD), along with plasma assisted chemical vapor deposition (PACVD) and ion beam assisted/enhanced deposition techniques.

A presently preferred method of establishing a polycrystalline diamond coating to make a dental article of the invention is plasma assisted chemical vapor deposition. Preferably, diamond-like amorphous hydrogen-free carbon coatings are applied to a substrate via a cathodic arc technique or an ion beam deposition, while diamond-like hydrogenated amorphous carbon coatings are applied via a plasma assisted chemical vapor deposition technique.

Preferably, the diamond-like coatings of the invention have a thickness in the range of about 0.05–30 microns, more preferably in the range of about 0.1–3 microns and most preferably in the range of about 0.1–0.3 microns. Polycrystalline diamond coatings of the articles of the invention preferably have a thickness in the range of about 0.1–50 microns, more preferably in the range of about 1–10 microns, and most preferably in the range of about 2–3 microns. Presently, the most preferred embodiment of the invention has a coating thickness of 0.2 microns and consists essentially of diamond-like amorphous hydrogen-free carbon.

Relatively thin diamond-like coatings are advantageous in that such coatings are less expensive than polycrystalline diamond coatings. Additionally, thicker coatings may adversely affect the article; for example, a relatively thick coating applied to an orthodontic arch wire substrate may adversely affect the amount of available force that can be utilized to shift the teeth for a wire of a given, overall cross-sectional area.

Preferably, surface contaminants, such as oxides or nitrides, on the substrate are removed by a cleaning process before the carbon deposition process is initiated. Ion sputtering techniques may be used for the cleaning process. When surface oxides are removed from metal substrates the incident carbon may react with the bare metal and form a carbide-like material between the substrate and the developing pure carbon coating. The carbide-like material forms a transition layer that may enhance the adhesion between a hard carbon coating and the substrate. In addition, a primer such as a layer of titanium may enhance the bond between the coating and the substrate.

The hard carbon coating of the dental article of the invention provides a diffusion resistant barrier that substantially reduces leaching of chromium and nickel from stainless steel and other alloys. In addition, the coating provides enhanced resistance to corrosion of metallic substrates when exposed to the oral environment. Further, hard carbon coatings are substantially clear, and as a result are more aesthetic than a hard coating made, for example, from carbide or nitride.

The hard carbon coated dental articles present a relatively low coefficient of friction, a particular advantage when the article is associated with sliding mechanics in orthodontic treatment. For example, when the coating 54 on the arch wire 50 is in engagement with the slots 18 of the bracket 10, reduced friction is presented to longitudinal sliding movement of the arch wire 50 relative to the bracket 10 in comparison to uncoated similar articles. Reduced friction permits the tooth associated with bracket 10 to more easily shift along the length of the arch wire 50 under the influence of induced forces as selected by the orthodontist.

SAMPLE PREPARATION

Test samples were made using a cathodic-arc deposition process to apply a diamond-like amorphous hydrogen-free carbon coating to substrates. The deposition process used was essentially the same as described in an article entitled "Properties of the Diamond-like Carbon Film Produced by the Condensation of a Plasma Stream with an RF Potential", authored by V. E. Strel'nitskii et al (Sov. Phys. Tech. Phys. 23 (2), February 1978). A DC bias of $-25$ to $-35$ volts was measured on the sample holder. The arc discharge was initiated with a mechanical striker and maintained at 100 amps with a Miller welding power supply (Intelliweld 650), operating in the current control mode. The arc voltage varied between 40 and 50 volts, and produced a carbon plasma which was the source of carbon for the coating. The plasma was transported to the substrates using a magnetic field with a magnitude ranging from 25 to 100 gauss.

Flat samples were prepared by mounting a flat substrate in a vacuum chamber of the deposition apparatus in an orientation such that a test surface of the sample was facing the carbon cathode. Orthodontic bracket substrates to make bracket samples were mounted in the test chamber by placing the tooth-facing side of the bracket base in a direction away from the carbon cathode such that the tiewings and arch wire slots faced the cathode. Orthodontic arch wire substrates for making coated arch wire samples were mounted in the vacuum chamber by clamping the ends of straight sections of arch wire in an orientation such that the longitudinal axis of the arch wire was perpendicular to the chamber axis (that extended in a direction from the midpoint of the arch wire substrate to the cathode). The arch wire substrates were secured to a plate that was rotated about the chamber axis.

Prior to coating each substrate, a Kauffman argon ion beam source (Commonwealth Scientific Corporation, 3 cm ion source) was directed to each substrate for approximately 5 minutes in order to sputter clean each substrate and remove surface oxides and other contaminants. An ion energy of 1000 volts and a beam current of 30 to 40 milliamps was used. The distance between the ion source and the sample was approximately 15 cm. Unless otherwise noted, each substrate was then exposed 12 times to the carbon plasma for five second intervals for a total deposition time of 60 seconds.

EXAMPLE 1

A 0.2 mm flat metal sheet made of an alloy having a relatively high nickel content (similar to alloys sold under the trademark "Permaloy") was cut into a square substrate measuring about 10 cm $\times$ 10 cm and coated according to the procedure set out in SAMPLE PREPARATION. The coated sample was then cut into two square test samples measuring about 1.3 cm $\times$ 1.3 cm.

A Perkin-Elmer Auger system (PHI Model No. 595) was used to obtain an Auger spectrum from each sample at various depths in the coating. Initially, the elemental composition of the near-surface region was determined. Next, the near-surface region was removed by sputtering with a 3,000 volt, 75 $\mu A/CM^2$ argon ion beam for 30 seconds. The elemental composition of the newly exposed near-surface region was determined from another Auger spectrum and recorded. The sputtering and Auger analysis cycle was repeated until the coating was removed from the substrate.

The concentration vs. sputtering time profiles (using a spline-fitting algorithm) for a control sample are set out in FIG. 6, wherein A is a curve representing carbon, B is a curve representing nickel and C is a curve representing chromium. Since each time interval of sputtering removed additional surface regions, the total sputtering time somewhat correlates to the depth of the surface of the sample that was removed. FIG. 6 is therefore somewhat representative of the relative concentrations of carbon, nickel and chromium at various depths in the sample.

Another sample was annealed at 250° C. for 24 hours in a gravity oven (Stabil-Therm, Model OV-12A, by Blue-M). A mercury thermometer protruded from the top of the oven and was used to monitor the temperature. The Auger spectrum was determined for the near-surface region of the annealed sample and again after exposure to ion beam sputtering in the manner described above in connection with the control sample, and the results are set out in FIG. 7 (where curves D, E, F represent carbon, nickel and chromium respectively).

Figure 7:
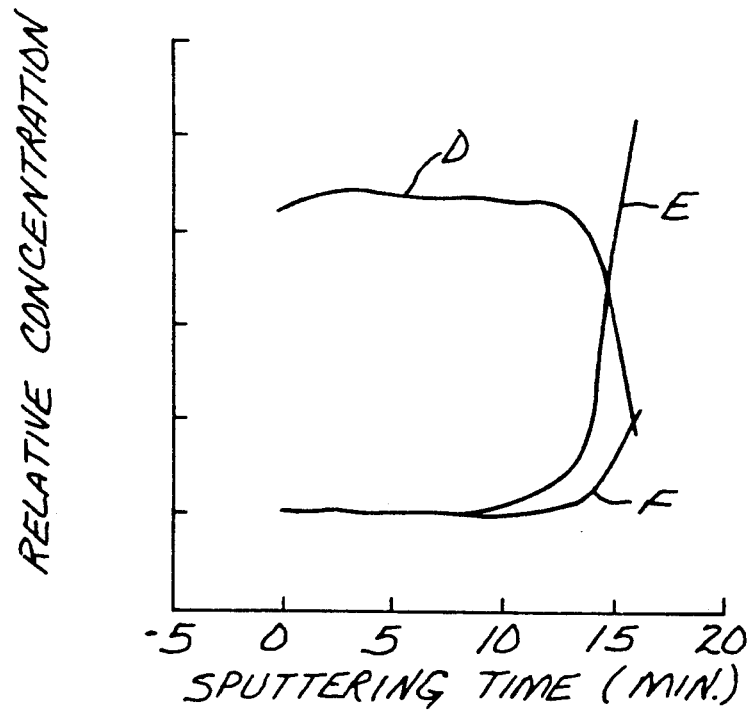

The data in FIGS. 6 and 7 show that the concentration of nickel and chromium is not greater in the annealed sample after any given sputtering time than the concentration of nickel and chromium in the non-annealed sample after the same sputtering time had elapsed. This shows that the coating presented a substantial barrier to the diffusion of nickel and chromium. Since diffusion is a thermally activated process, it is concluded that the hard carbon coating of a dental article would substantially prevent chromium and nickel from diffusing to the surface and contacting the patient's saliva or oral tissue when subjected to temperatures normally encountered in the oral cavity.

EXAMPLE 2

Sliding friction was compared between various combinations of uncoated and coated orthodontic brackets and arch wires. Coated brackets were prepared according to SAMPLE PREPARATION, using a central maxillary ceramic bracket ("Transcend" brand brackets, Cat. #2001-801, 3M Unitek) made from alumina, and a metal injection molded upper right cuspid, miniature twin bracket (Cat. #017-206, 3M Unitek) made from ASTM Type 630 (17Cr-4Ni) stainless steel. Coated arch wire samples were prepared according to SAMPLE PREPARATION from an 18 cm section of 0.43 mm ×0.63 mm (0.017 in. ×0.025 in.) stainless steel arch wire ("Hi-T II Twist Flex" brand arch wire; Cat. #256-725; 3M Unitek) and nickel-titanium arch wire (Nitinol SE brand arch wire, Cat. #297-002, 3M Unitek).

Elastomeric ligatures ("Alastic" brand ligatures, Cat. #406-011, 3M Unitek) were used to ligate the arch wires into the arch wire slots of the brackets. One end of each arch wire was attached in turn to an Instron Model 1123 tensile testing apparatus. The bracket was mounted in an orientation such that the arch wire was pulled in a direction aligned with the portion of the wire ligated to the bracket.

Each arch wire was pulled by the Instron apparatus through the arch wire slot of the corresponding bracket at a rate of 0.5 mm per minute. The force in grams required to pull the arch wire a total distance of 0.152 mm was recorded on a strip chart recorder having a chart speed of 25.4 cm per minute. The work done to overcome friction was determined and is set out in Table I for the various bracket/arch wire combinations.

explanation is known for the higher frictional force as noted in Table I between a coated metal bracket and an uncoated stainless steel arch wire.

EXAMPLE 3

Potentiodynamic polarization resistance measurements were made to compare the corrosion resistance of stainless steel samples to stainless steel samples coated with hard carbon. A sheet of stainless steel, Type SS430, was cut into three flat samples of about 1.9 cm×1.9 cm×1.9 mm. One sample was left uncoated and two samples were coated in accordance with the procedures set out in SAMPLE PREPARATION.

The testing procedure was carried out according to ASTM standard practices G3-89, G59-78 (1984), and G102-89 except that no hydrogen flow was employed. Contact area of the sample with the electrolyte solution was limited by a polytetrafluoroethylene O-ring to a circular area of 1.0 cm$^2$.

Experiments were run using a flat electrode cell (EG&G PARC) with a silver/silver nitrate reference and 1.0N sulfuric acid bridge solution. Software sold under the trademark "Soft Corr" (EG&G PARC M342) was used on an IBM PS/2 Model 70 computer to control a potentiostat (EG&G PARC M273).

Results of the tests indicated a current density of 0.28 $\mu/cm^2$ for the uncoated sample, 0.05 $\mu/cm^2$ for the sample coated for 17 seconds, and 0.02 $\mu/cm^2$ for the sample coated for 30 seconds. The data show that the coated samples had significantly greater resistance to corrosion than the uncoated sample, and that the corrosion resistance may increase with increased thickness of the coating.

EXAMPLE 4

Wear testing was undertaken to determine wear characteristics of hard carbon coated and uncoated samples along with wear characteristics of opposing tooth enamel in an apparatus simulating the oral environment. Two flat samples of polycrystalline alumina (Ceralloy #514F) were obtained and one sample was coated with a hard carbon coating according to SAMPLE PREPARATION.

Wear testing was carried out using the apparatus and procedure described in an article entitled "An Artificial

TABLE I

| | WORK DONE TO OVERCOME FRICTION, IN GM-CM | | | |
|---|---|---|---|---|
| | Ceramic Bracket with Stainless Steel Arch Wire | Ceramic Bracket with Nickel—Titanium Arch Wire | Metal Bracket with Stainless Steel Arch Wire | Metal Bracket with Nickel—Titanium Arch Wire |
| Uncoated Bracket Uncoated Arch Wire | 1227 | 1422 | 889 | 1276 |
| Uncoated Bracket Uncoated Arch Wire | 828 | 1295 | 1007 | 1180 |
| Uncoated Bracket Uncoated Arch Wire | 782 | 1229 | 875 | 1246 |
| Uncoated Bracket Uncoated Arch Wire | 807 | 1066 | 887 | 1228 |

The data show that significantly less frictional force is encountered between ceramic brackets and either stainless steel or nickel-titanium arch wire when either the bracket or the arch wire is coated with a hard carbon coating. Slight improvement in the relative frictional force between the metal bracket and the nickel-titanium arch wire was observed when either was coated. No significant improvement in the frictional force between a metal bracket and a stainless steel arch wire was observed when either or both was coated. No Oral Environment for Testing Dental Materials" by R. DeLong and W. Douglas (IEEE Transactions on Biomedical Engineering, Vol. 38, No. 4, April 1991 pp. 339-345). The apparatus was utilized for 300,000 cycles.

No wear was observed on either the hard carbon coated ceramic sample or the uncoated sample. However, a volume decrease on the enamel was determined to be 0.0402 ±0.0075 mm$^3$ when opposed to the uncoated sample, and 0.0308±0.0062 m$^3$ when opposed to the hard carbon coated sample. The volume change was determined using a three dimensional contact stylus digitizing profiliometer system.

The data show that the wear on opposing enamel was slightly less for the hard carbon coated sample than the uncoated sample, although the difference was slight and may or may not be significant.

We claim:

1. A dental article having a hard carbon coating wherein said article comprises an orthodontic archwire.

2. The article of claim 1, wherein the coating comprises polycrystalline diamond.

3. The article of claim 1, wherein said coating comprises diamond-like amorphous hydrogen-free carbon.

4. The article of claim 1, wherein said coating comprising diamond-like hydrogenated amorphous carbon.

5. The article of claim 1 including a substrate comprising a metal alloy.

6. The article of claim 5, wherein said metal alloy comprises stainless steel.

7. The article of claim 1, wherein the coating has a thickness in the range of about 0.05 to 30 microns.

8. The article of claim 1, wherein said coating has a thickness in the range of about 0.1 to 3 microns.

9. The article of claim 1, wherein said coating has a thickness in the range of about 0.1 to 0.3 microns.

10. The article of claim 1, wherein said coating comprises diamond-like carbon and has a thickness in the range of about 0.1 to 3.0 microns.

11. The article of claim 1, wherein said coating comprises polycrystalline diamond and has a thickness in the range of about 1 to 10 microns.

12. The article of claim 1, wherein said coating is substantially clear.

* * * * *